United States Patent
Suares et al.

(10) Patent No.: US 6,531,116 B1
(45) Date of Patent: Mar. 11, 2003

(54) TREATMENT REGIME FOR SKIN

(75) Inventors: Alan Suares, Cheshire, CT (US); Susan Nettesheim, New York, NY (US); Michael Indursky, Fairfield, CT (US); Peter Bertolini, Shelton, CT (US)

(73) Assignee: Chesebrough-Pond's USA Co., division of Conopco, Inc., Greenwich, CT (US)

( * ) Notice: Subject to any disclaimer, the term of this patent is extended or adjusted under 35 U.S.C. 154(b) by 963 days.

(21) Appl. No.: 09/177,695

(22) Filed: Oct. 22, 1998

Related U.S. Application Data

(62) Division of application No. 08/670,389, filed on Jun. 25, 1996, now Pat. No. 5,914,116.

(51) Int. Cl.⁷ .............................................. A61K 7/027
(52) U.S. Cl. .................... 424/59; 424/401; 514/844; 514/845; 514/846
(58) Field of Search .................. 424/401, 59; 514/844, 514/845, 62, 846

(56) References Cited

U.S. PATENT DOCUMENTS

| | | |
|---|---|---|
| 628,888 A | 7/1899 | Kirby |
| 880,082 A | 2/1908 | Kendrick |
| 2,077,219 A | 4/1937 | Conner |
| 2,326,414 A | 8/1943 | Thompson |
| 2,488,611 A | 11/1949 | Stallings |
| 2,645,375 A | 7/1953 | Topfer |
| 2,940,589 A | 6/1960 | Silverman |
| 3,067,896 A | 12/1962 | Berg et al. |
| 3,217,915 A | 11/1965 | Weygandt |
| 3,348,716 A | 10/1967 | Nakata |
| 3,476,286 A | 11/1969 | Steffens |
| 3,826,359 A | 7/1974 | Brecher |
| 4,197,316 A | 4/1980 | Yu et al. |
| 4,234,599 A | 11/1980 | Van Scott et al. |
| 4,424,234 A | 1/1984 | Alderson et al. |
| 4,517,815 A | 5/1985 | Basso |
| 4,595,099 A | 6/1986 | Zaruba et al. |

(List continued on next page.)

FOREIGN PATENT DOCUMENTS

| | | |
|---|---|---|
| CH | 585 647 | 10/1974 |
| DE | 29 04 478 | 2/1979 |
| DE | 39 11 089 | 4/1989 |
| EP | 0 318 834 | 6/1989 |
| EP | 0 345 082 | 12/1989 |
| EP | 0 501 714 | 9/1992 |
| GB | 2 231 782 | 11/1990 |
| NL | 9301506 | 4/1995 |
| WO | 94/06405 | 3/1994 |

OTHER PUBLICATIONS

Colt's Plastics Co., Inc.—Product Sheet (1994).
New York times, Apr. 11, 1948, Section 1, p. 64, Jacqueline Cochran "Perk–Up" set.
Pond's "Prevent & Correct" Cream—Advertising photo of product which was launched in USA in Oct., 1995.

Primary Examiner—Thurman K. Page
(74) Attorney, Agent, or Firm—Milton L. Honig

(57) ABSTRACT

A method for a skin treatment regime and a respective product is provided which cosmetically improves human skin. The product includes a first composition containing at least one active and functioning to impart a first benefit to the skin. A second composition is provided which includes a second different active and imparts a second benefit to the skin. The first and second compositions are stored in respective separate containers, which nevertheless are joined together for reminding a consumer to use the compositions in tandem and to facilitate in one sale all necessary elements of a suggested regime. Packaging suitable for this purposes can be a series of stackable jars releasably lockable together through a threaded screw arrangement one above the other.

10 Claims, 1 Drawing Sheet

U.S. PATENT DOCUMENTS

| | | |
|---|---|---|
| 4,598,832 A | 7/1986 | Alonso |
| 4,949,874 A | 8/1990 | Fiedler et al. |
| 5,083,674 A | 1/1992 | Clark |
| 5,306,486 A | 4/1994 | McCook et al. |
| 5,339,975 A | 8/1994 | Stoner |
| 5,382,432 A | 1/1995 | McCook et al. |
| 5,409,128 A | 4/1995 | Mitchell |
| 5,914,116 A * | 6/1999 | Suares et al. ............... 424/401 |

* cited by examiner

TREATMENT REGIME FOR SKIN

This is a divisional of Ser. No. 08/670,389 filed Jun. 25, 1996 now U.S. Pat. No. 5,916,116.

BACKGROUND OF THE INVENTION

1. Field of the Invention

The invention concerns a skin treatment regime formed with separate containers each storing a composition functioning to impart a benefit to the skin.

2. The Related Art

Dual purpose single formulation cosmetic products are quite handy and popular. Examples of 2-in-1 commercial formulations are cleanser & moisturizer and shampoo & conditioner products. Unfortunately, single formulations often compromise the performance of the severally combined actives.

A response to this problem has been the development of skin treatment regimes. Two or more different cosmetic compositions are employed in these regimes and applied to the skin in sequential order. Illustrative commercial treatment regime compositions are cleansers, moisturizers, toners and facial foundations.

When a skin treatment regime requires multi-composition use, there have been problems with consumer education and discipline. Education is particularly a problem in mass market outlets where a cosmetic knowledgeable sales staff is generally absent. A customer may purchase one product in a treatment regime but may be uninformed with respect to a necessary complementary regime product. Even a somewhat educated customer may select the wrong complementary product. Most frustrating is when a totally educated customer discovers that the store either does not carry the complementary product or is temporarily out of stock.

Even when a customer has been educated and supplied with proper products, the products may become separated at home. Moreover, the necessary reinforcement of use according to a regime may no longer be present.

Accordingly, it is an object of the present invention to provide a cosmetic product for a skin treatment regime that assists the consumer in maintaining the regime.

It is another object of the present invention to provide a cosmetic product with multi-compositions for a skin treatment regime that ensures the recommended compositions are all provided to the consumer in a single sale.

Still another object of the present invention is to provide a cosmetic product for a skin treatment regime that daily serves as a reminder to the consumer as to the proper utilization of component compositions.

Yet another object of the present invention is to provide a cosmetic product for a skin treatment regime that maintains each of the compositions together in a unit to avoid separation and misplacement within a consumer's home.

SUMMARY OF THE INVENTION

A method is provided for cosmetically improving human skin through a treatment regime including:

providing a first composition containing at least one first active within a first pharmaceutically acceptable carrier, the first composition functioning to impart a first benefit to the skin;

providing a second composition containing at least one second active within a second pharmaceutically acceptable carrier, the second composition functioning to impart a second benefit to the skin, the first and second actives and benefits being different from one another;

storing the first composition in a first container;

storing the second composition in a second container, the first and second containers being joined together;

applying the first composition to the skin to achieve the first benefit; and applying the second composition to the skin after application of the first composition to achieve the second benefit.

Preferably the first and second containers are fitted together in a releasably. joinable manner, most preferably fitted together with a coupling mechanism such as a screw thread arrangement. Advantageously the first and second containers are jars stacked one above the other and releasably locked together through the coupling mechanism.

Also provided is a skin treatment regime product including:

a first composition containing at least one first active within a first pharmaceutically acceptable carrier, the first composition functioning to impart a first benefit to the skin;

a second composition containing at least one second active within a second pharmaceutically acceptable carrier, the second composition functioning to impart a second benefit to the skin;

a first container for storing the first composition; and a second container for storing the second composition, the first and second containers being joined together, preferably in a releasably joined. manner.

BRIEF DESCRIPTION OF THE DRAWING

The above features, advantages and objects of the present invention will more fully be appreciated through the following detailed discussion, reference being made to the drawing in which.

DETAILED DESCRIPTION

Now it has been found that a skin treatment regime requiring application of a multiple of separate compositions can be sold to a consumer as a unit, serve as a reminder for joint usage and also educate the consumer in proper application thereof. These advantages are achieved through disposition and sale of the respective compositions in respective containers wherein the two containers are joined together.

Figure 1:
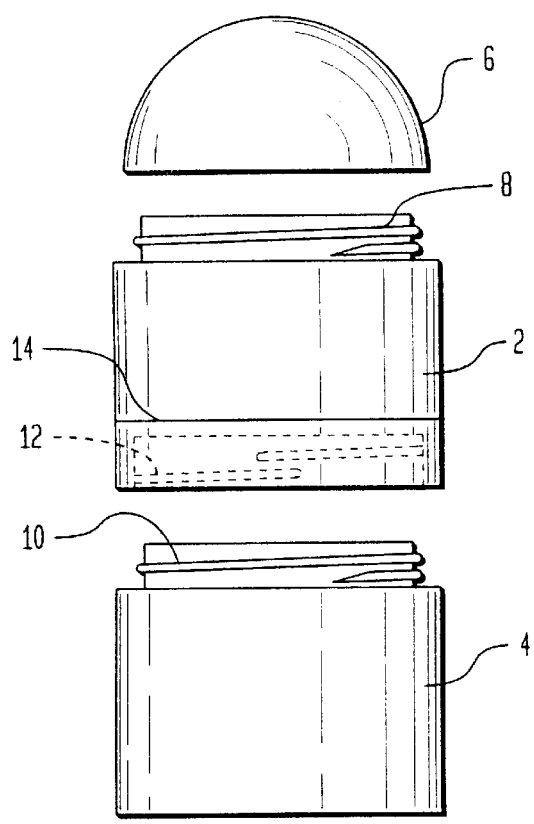
FIG. 1 is a perspective view of a stacked pair of jars releasably lockable one on top another.

FIG. 1 illustrates a first embodiment of a dispensing package including a first container or jar 2, a second container or jar 4 and a domed cap 6. First container 2 is fitted at an open end thereof with a threaded male screw 8 that can lockingly engage cap 6 for closure of that jar. A first composition incorporating a first active is stored within container 2.

Second container 4 at an open end thereof is also fitted with a threaded male screw 10. A second composition is stored within the second container. Threaded male screw 10 is lockingly joinable with a threaded female screw 12 arranged below a closed bottom end 14 of the first container 2. In a preferred embodiment, the first container 2 storing first composition has an outer color different from that of the outer color of the second container 4. For instance, if the first and second compositions are respectively intended for day and night use, the first container 2 may be colored predominantly white (day formula) and the second container 4 may be colored predominantly black (night formula). The term "predominantly" means greater than 50% of the surface area of outer walls of the container. Color coding provides the consumer with an educational signal for proper use of the cosmetic product.

Figure 2:
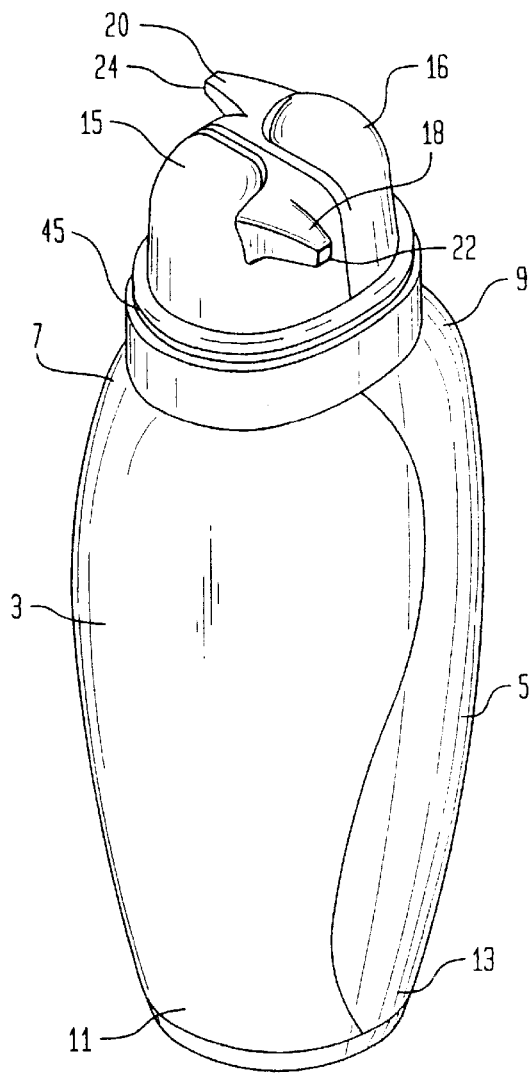
FIG. 2 is a perspective view of a dual compartment package with pump mechanisms associated with each compartment for dispensing respective compositions.

FIG. 2 illustrates a second embodiment of a dispensing package suitable for a lotion or other relatively non-viscous liquid cosmetic composition. This embodiment of the dispenser includes a first and second container 3, 5 having respective first and second top ends 7, 9 and first and second bottom ends 11, 13. The top ends are open and the bottom ends are closed. First and second pump mechanism 15, 16 with respective dispensing nozzles 18, 20 having dispensing openings 22, 24 are positioned over the top ends of their respective containers. Openings 22, 24 of the dispensing nozzles are oriented in a direction 180° opposite one another. It is an important feature that the dispensing nozzle openings are oriented so that simultaneous pressing of both pump mechanisms is not suggested to a consumer. A manner for avoiding this orients the dispensing nozzle openings at an angle of at least 60° C., most preferably 180° apart from one another.

Table 1 lists various types of cosmetic compositions which may serve as the first and second compositions referred to above. These are described in terms of their major benefit to the skin.

TABLE I

| FIRST COMPOSITION | SECOND COMPOSITION |
| --- | --- |
| Cleanser | Moisturizer |
| Cleanser | Anti-acne preparation |
| Cleanser | Moisturizer |
| Cleanser | Facial Foundation |
| Moisturizer | Toner |
| Cleanser | Skin Lightener |
| Self-Tanner | Cleanser |
| Cleanser | Sunscreen |
| Skin Lightener | Sunscreen |
| Sunscreen | Anti-wrinkle Cream |
| Moisturizer | Sunscreen |

It is to be understood that this invention is not limited to just two compartments or that these contain only two separate compositions. For instance, there may be anywhere from three to six additional compartments, each containing their respective skin treatment regime. An example would be a package with a stack of four jars similar to that of FIG. 1 each respectively containing a moisturizer, cleanser, toner and facial foundation. It is to be emphasized that the assortment of compositions are intended to be used in combination with one another for a treatment regime. This would contrast with, for instance, a travel kit where a variety of cosmetics could be stored but each functioning independently such as a series of colored powders or the like.

At least one active material will be incorporated into each of the separate compositions, the active being present as the primary functional ingredient to deliver the benefit for which the composition is applied.

Sunscreen compositions will of course incorporate a sunscreen as the active material. The term "sunscreen" is used to denote ultraviolet ray-blocking compounds inhibiting absorption within the wavelength region between 290 and 420 nm. These compounds may either be organic or inorganic. The organic compounds are preferred. When the sunscreen is inorganic and serves as the sole sun protective substance, it should be present at levels ranging from about 5 to 30%, preferably from about 8 to 15% by weight.

Typical inorganic sunscreens include titanium dioxide, zinc oxide, iron oxide and combinations thereof. Most preferred is titanium dioxide, especially having an average particle size no higher than 700 nm, preferably no higher than 200 nm, optimally less than 35 nm.

Organic sunscreens may be classified into five groups based upon their chemical structures: para-amino benzoates; salicylates; cinnamates; benzophenones; coumarins; azoles and miscellaneous chemicals including menthyl anthralinate. Also polymeric particles may be useful such as polyethylene and polyamides. Organic sunscreen compound will range in amount anywhere from about 0.1 to 25%, optimally from about 1 to 15%, most preferably from about 5 to 10% by weight.

Anti-wrinkle compositions will usually contain one or more actives such as alpha-hydroxycarboxylic acids or salts thereof, beta-hydroxycarboxylic acid or salts thereof, retinoids, ceramides and combinations thereof.

A wide variety of $C_2$–$C_{30}$ alpha-hydroxycarboxylic acids may be employed. Suitable examples of which include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosdnoic acid
α-hydroxyhexacosanoic acid, and
α-hydroxyoctacosanoic acid Particularly preferred from the above list are α-hydroxyethanoic acid (commonly known as glycolic acid), α-hydroxypropanoic acid (commonly known as lactic acid) and α-hydroxyoctanoic acid (commonly known as α-hydroxycaprylic acid or HCA).

Suitable $C_2$–$C_{30}$ beta-hydroxycarboxylic acids or salts are usually selected from derivatives of salicylic acid, especially esters thereof.

For purposes of this invention, the term α-hydroxycarboxylic acids and beta-hydroxycarboxylic acids are intended to include not only the acid form but also salts thereof. Typical salts are the alkalimetal, ammonium and $C_2$–$C_{60}$ ammonium salts thereof. Particularly preferred are the sodium, potassium,. triethanolammonium, polyethyleneimine and ammonium salts. Combinations of all the foregoing may be present in the compositions. Amounts of the α or β-hydroxycarboxylic acid or salt thereof may range from about 0.01 to about 15%, preferably from about 0.1 to about 12%, optimally from about 0.5 to about 9% by weight.

Suitable retinoids are retinol, retinoic acid or the $C_1$–$C_{20}$ esters of retinol and 1E retinoic acid. Illustrative ceramides are Ceramide 1, Ceramide 2, Ceramide 3 and Ceramide 6. Pseudoceramides may also be useful. Levels of retinoids and ceramides may range anywhere from 0.00001 to 2%, preferably from 0.0001 to 0.1% by weight.

Surfactants are included as actives for cleanser compositions of this invention. These may be selected from nonionic, anionic, cationic or amphoteric emulsifying agents. They may range in amount anywhere from about 0.1 to 30% by weight. Illustrative of the nonionic surfactants are alkoxylated compounds based upon $C_8$–$C_{22}$ fatty alcohols, $C_8$–$C_{22}$ fatty acids and sorbitan.

Skin lighteners may include such actives as kojic acid, niacinamide, hydroquinone and derivatives of these materials. Amounts may range anywhere from 0.001 to 10% by weight.

Self-tanning compositions will usually include an active such as dihydroxyacetone, possibly in combination with amines and/or amino acids. Amounts of the combined actives may range from 1% to 30% by weight, Anti-acne preparations will usually include an active selected from the group consisting of benzoyl peroxide, an alpha-hydroxycarboxylic acid, salicylic acid, retinoids and their derivatives. Amounts of these materials may range anywhere from 0.1 to 30% by weight of the composition.

The first, second or any other compositions of the present invention may be solid or liquid, aqueous or anhydrous and opaque or transparent.

A pharmaceutically acceptable carrier is ordinarily utilized to deliver the active components of the first and second compositions. Most preferably, cosmetic compositions of this invention will be in emulsion form. By definition, an emulsion is a dispersed system containing at least two immiscible liquid phases, one of which is dispersed in the form of small droplets throughout the other. Water and oil are the most common immiscible phases. An emulsion in which oil is dispersed as droplets throughout the aqueous phase is termed an oil-in-water emulsion. When water is the dispersed phase and an oil is the dispersion medium, a water-in-oil emulsion exists. Contemplated within the scope of this invention are emulsions in the form of lotions and creams of both types of emulsions, those where the water phase is continuous and those where the oil phase is continuous. The amount of these phases may range from about 99:1 to 1:99 by weight.

The term "pharmaceutically acceptable carrier" according to this invention includes emollients, humectants, thickeners, silicones and water. Total amount of the carrier may range from about 30 to about 99.9%, preferably from about 50.to about 90%, optimally from-about 70 to about 85% by weight.

A variety of oily emollients may be employed in the compositions of this invention. These emollients may be selected from one or more of the following classes:

1. Hydrocarbon oils and waxes. Examples thereof are mineral oil, petrolatum, paraffin, ceresin, ozokerite, microcrystalline wax, polyethylene, and perhydrosqualene.
2. Triglyceride esters such as vegetable and animal fats and oils. Examples include castor oil, cocoa butter,. safflower oil, cottonseed oil, corn oil, olive oil, cod liver oil, almond oil, avocado oil, palm oil, sesame oil, squalene, and maleated soybean oil.
3. Acetoglyceride esters, such as acetylated monoglycerides.
4. Ethoxylated glycerides, such as ethoxylated glyceryl monostedrate.
5. Alkyl esters of fatty acids having 10 to 22 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
6. Alkenyl esters of fatty acids having 10 to 22 carbon atoms. Examples thereof include oleyl myristate, oleyl stearate, and oleyl oleate.
7. Fatty acids having 10 to 22 carbon atoms. Suitable examples include pelargonic, lauric, myristic, palmitic, stearic, isostearic, hydroxystearic, oleic, linoleic, ricinoleic, arachidic, behenic, and erucic acids.
8. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecanyl alcohols are examples of satisfactory fatty alcohols.
9. Fatty alcohol ethers. Ethoxylated fatty alcohols of 10 to 22 carbon atoms including the lauryl, cetyl, stearyl, isostearyl, oleyl, and cholesterol alcohols, having attached thereto from 1 to 50 ethylene oxide groups or 1 to 50 propylene oxide groups.
10. Ether-esters such as fatty acid esters of ethoxylated fatty alcohols.
11. Lanolin and derivatives, Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.
12. Polyhydric alcohol esters, Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 mono- oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid esters, sorbitan fatty acid esters, and polyoxyethylene sorbitan fatty acid esters are satisfactory polyhydric alcohol esters.
13. Wax esters such as beeswax, spermaceti, myristyl myristate, stearyl stearate.
14. Beeswax derivatives, e.g. polyoxyethylene sorbitol beeswax. These are reaction products of beeswax with ethoxylated sorbitol of varying ethylene oxide content, forming a mixture of ether esters.
15. Vegetable waxes including carnauba and candelilla waxes.
16. Phospholipids such as lecithin and derivatives,
17. Sterols, Cholesterol, cholesterol fatty acid esters are examples thereof.
18. Amides such as fatty acid amides, ethoxylated fatty acid amides, solid fatty acid alkanolamides.

Amounts of the above listed emollients may range anywhere from about 0.5 to about 80% by weight of the total composition. Preferably the amounts of these emollients will range from about 1 to about 25%, optimally between about 5 and 15% by weight.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol,, 1,3-butylene glycol, 1,2,6-hexanetriol, ethoxylated glycerol, propoxylated glycerol and mixtures thereof. For best results the humectant is preferably glycerol. The amount of humectant may range anywhere from 0.1 to 40%, preferably between 1 and 15% by weight of the composition.

For improved lubricity, there may also be included one or more silicone oils or fluids which may be selected from a dimethyl polysiloxane, a methylphenyl polysiloxane and an alcohol-soluble silicone glycol copolymer. Preferred siloxanes include dimethyl polysiloxane (CTFA name: dimethicone), a polysiloxane end-blocked with trimethyl units and polydimethylcyclosiloxane, (CTFA name: cyclomethicone). The preferred siloxanes exhibit a viscosity from about 2 to 50 centistokes at 25° C. Amounts of the silicones can range from about 0.1 to 80% by weight of the compositions, preferably from about 1 to 20% by weight.

Both first and second compositions of the invention can also include thickeners/viscosifiers in amounts from about 0.01 to about 10% by weight of the composition. As known to those skilled in the art, the precise amount of thickeners can vary depending upon the consistency and thickness of the composition which is desired. Exemplary thickeners are magnesium aluminum silicate (Veegum®), guar gums (such as Jaguar HP-120®), xanthan gum, sodium carboxymethyl cellulose, hydroxyalkyl and alkyl celluloses, and cross-linked acrylic acid polymers such as those sold by B. F. Goodrich under the Carbopol® trademark.

Preservatives can desirably be incorporated into both the first and second compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

When present, the amount of water in a composition may range anywhere from about 1 to about 99%, preferably from about 20 to about 90%, optimally between about 40 and 70% by weight.

In a preferred aspect of the present invention, the first and second compositions will each have at least five components in common. Moreover, the five components will be present at essentially identical concentrations in both the first and second compositions.

The following examples will more fully illustrate the composition embodiments of this invention. All parts, percentages and proportions referred to herein and in the appended claims are by weight unless otherwise indicated.

EXAMPLE 1

In a treatment regime to prevent and correct skin damage, a first composition was employed wherein sunscreens were utilized as the actives and a sun protection benefit was imparted to the skin. This composition is intended for daytime protection. As part of the regime, a corrective anti-wrinkle preparation was applied at nighttime with alpha-hydroxycarboxylic acids utilized as the actives to correct damage done by sunlight. This second, anti-wrinkle composition was applied for nighttime wear.

TABLE II

SUNSCREEN (PREVENT) COMPOSITION

| COMPONENT | WEIGHT % |
|---|---|
| Parsol MCX ® | 4.00 |
| Stearic Acid | 3.00 |
| Finsolv TN ® | 3.00 |
| Butylene Glycol | 2.00 |
| Glycerin | 2.00 |
| MYRJ 59 ® | 2.00 |
| Uvinul M-40 ® | 2.00 |
| Crodamol ISNP ® | 2.00 |
| Glycerol Monostearate | 1.50 |
| Stearyl Alcohol | 1.50 |
| Glycolic Acid (70%) | 1.40 |
| Triethanolamine (99%) | 1.20 |
| Lactic Acid | 1.15 |
| Magnesium Aluminum Silicate | 1.00 |
| Arlacel 60 ® | 1.00 |
| Silicone 1401 ® | 0.80 |
| Disodium EDTA | 0.50 |
| Jaguar Hp-120 ® | 0.50 |
| Cholesterol | 0.30 |
| Ammonia (Aqueous 26BE) | 0.30 |
| Fragrance | 0.30 |
| Tween 80 ® | 0.30 |
| Polyethyleneimine | 0.25 |
| Methylparaben | 0.15 |
| Vitamin E Acetate | 0.10 |
| Propylparaben | 0.10 |
| Hydroxycaprylic Acid | 0.10 |
| Vitamin A Palmitate | 0.10 |
| Water | qs |

TABLE III

ANTI-WRINKLE (CORRECT) COMPOSITION

| COMPONENT | WEIGHT % |
|---|---|
| Glycolic Acid (70%) | 5.74 |
| Butylene Glycol | 3.00 |
| Hetester ® FAO/Fine | 3.00 |
| Stearic Acid | 3.00 |
| Finsolv TN ® | 2.50 |
| Ceraphyl 230 ® | 2.50 |
| Ammonia (Aqueous 26BE) | 2.20 |
| Glycerin | 2.00 |
| Myrj 59 ® | 2.00 |
| Polyethyleneimine | 2.00 |
| Stearyl Alcohol | 1.50 |
| Glycerol Monostearate | 1.50 |
| Triethanolamine (99%) | 1.20 |
| Magnesium Aluminum Silicate | 1.00 |
| SE 700 | 1.00 |
| Silicone Fluid 10 | 1.00 |
| Arlacel 60 ® | 1.00 |

TABLE III-continued

ANTI-WRINKLE (CORRECT) COMPOSITION

| COMPONENT | WEIGHT % |
|---|---|
| Dow Corning 1401 ® | 0.80 |
| Jaguar HP-120 ® | 0.50 |
| Disodium EDTA | 0.50 |
| Sodium Stearoyl Lactylate | 0.50 |
| Cholesterol | 0.30 |
| Fragrance | 0.30 |
| Tween 80 ® | 0.30 |
| Methylparaben | 0.15 |
| Antifoam Emulsion | 0.10 |
| Vitamin E Acetate | 0.10 |
| Propylparaben | 0.10 |
| Hydroxycaprylic Acid | 0.10 |
| Vitamin A Palmitate | 0.10 |
| Bisabolol | 0.10 |
| Water | qs |

EXAMPLE 2

This example illustrates a combination of a cleanser and skin-ligthening regime. The cleanser of Table IV is first applied to the skin. The face is then washed with water, dried and then the skin-lightening preparation of Table V was applied.

TABLE IV

CLEANSER

| COMPONENT | WEIGHT % |
|---|---|
| Glycerin | 1.50 |
| Polyoxyethylene hydrogenated castor oil | 1.50 |
| Sorbitan stearate | 1.00 |
| Squalane | 10.00 |
| Dipropylene glycol | 5.00 |
| Genistein | 0.10 |
| Water | qs100.00 |

TABLE V

SKIN-LIGHTENER

| COMPONENT | WEIGHT % |
|---|---|
| Polysorbate 80 | 1.00 |
| Ethyl alcohol | 3.00 |
| Polyethylene glycol-600 | 5.00 |
| Citric acid | 0.03 |
| Sodium citrate | 0.20 |
| 1-o-Ethyltetraacetylglucosamine | 0.10 |
| Methylparaben | 0.10 |
| Fragrance | qs |
| Water | qs 100.00 |

EXAMPLE 3

This example illustrates a combination of a moisturizer and an anti-wrinkle cream regime. First the moisturizer is applied to the skin. Thereafter the anti-wrinkle cream is used to cover the moisturizer. Tables VI and VII illustrate these compositions.

TABLE VI

MOISTURIZER

| COMPONENT | WEIGHT % |
|---|---|
| Glycerin α-methyl ether | 10.00 |
| Citric acid | 0.03 |
| Sodium citrate | 0.07 |
| Polyoxyethylene oleyl ether | 0.50 |
| Ethyl alcohol | 5.00 |
| Methylparaben | 0.10 |
| Fragrance | qs |
| Water | qs100.00 |

TABLE VII

ANTI-WRINKLE CREAM

| COMPONENT | WEIGHT % |
|---|---|
| Polysorbate 60 | 3.00 |
| Sorbitan stearate | 3.00 |
| Cetyl alcohol | 1.00 |
| Mineral oil | 8.00 |
| Glycerin | 1.00 |
| Methylparaben | 0.10 |
| Ammonium lactate | 3.70 |
| Water | qs 100.00 |

EXAMPLE 4

This example illustrates a regime wherein a cleanser and a toner are applied to the face. First the cleanser is applied. After at least a five minute scrub, the toner is placed on the face. Tables VIII and IX illustrate these compositions.

TABLE VIII

CLEANSER

| PHASE | INGREDIENT | WEIGHT % |
|---|---|---|
| A | Deionized Water | 43.03 |
|   | Allantoin | 0.50 |
|   | Methylparaben | 0.20 |
|   | Ethylenediaminetetraacetic acid | 0.02 |
|   | Imidazolidinyl urea | 0.30 |
| B | Propylene glycol | 6.00 |
|   | Magnesium aluminum silicate | 1.00 |
| B | Sodium carboxymethyl cellulose | 0.10 |
| C | Stearyl alcohol | 1.50 |
|   | Cetyl alcohol | 3.00 |
|   | Glyceryl monostearate and Polyoxyethylene (100) monostearate | 2.00 |
|   | Polyoxyethylene (10) soya sterols | 2.50 |
|   | Polyoxyethyene (3) myristyl ether myristate | 15.00 |
|   | Squalane | 15.00 |
|   | Silicone Fluid 344 ® | 12.00 |
|   | Propylparaben | 0.10 |
|   | Butylparaben | 0.10 |
| D | Deionized Water | 0.50 |
|   | Dowicil 200 ® | 0.15 |

TABLE IX

TONER

| PHASE | INGREDIENT | WEIGHT % |
|---|---|---|
| A | Deionized water | 10.00 |
|   | Carbopol 941 ® | 0.10 |

TABLE IX-continued

TONER

| PHASE | INGREDIENT | WEIGHT % |
|---|---|---|
| B | Deionized Water | 82.90 |
|   | Glycerin | 2.00 |
|   | Methylparaben | 0.20 |
|   | Allantoin | 0.30 |
|   | Imidazolidinyl urea | 0.30 |
| C | Acetylated polyoxyethylene (10) lanolin alcohol | 1.00 |
|   | Cetyl/stearyl 2-ethylhexanoate | 1.00 |
|   | Propylparaben | 0.10 |
| D | Deionized water | 2.00 |
|   | 98% Triethanolamine | 0.10 |

Although this invention has been described with reference to specific Examples and package embodiments, it will be apparent to one skilled in the art that various modifications may be made thereto which fall within the scope and purview of the invention.

What is claimed is:

1. A method for cosmetically improving human skin through a treatment regime comprising:

providing a first composition containing at least one first active within a first pharmaceutically acceptable carrier, the first composition functioning to impart a first benefit to the skin;

providing a second composition containing at least one second active within a second pharmaceutically acceptable carrier, the second composition functioning to impart a second benefit to the skin, the first and second actives and benefits being different from one another;

storing the first composition in a first container;

storing the second composition in a second container, the first and second containers being joined together;

instructing consumers by placing on the containers or packaging associated therewith instructions on use of the first and second compositions in a sequential manner to achieve the first and second benefits in a treatment regime, the first and second compositions being complementary products;

applying the first composition to the skin to achieve the first benefit; and applying the second composition to the skin after application of the first composition to achieve the second benefit.

2. A method according to claim 1 wherein the first and second containers are each fitted with a means for coupling same to one another.

3. A method according to claim 2 wherein the means for coupling is a threaded screw.

4. A method according to claim 2 wherein the first and second containers are stacked one above the other and releasably locked together by the means for coupling.

5. A method according to claim 1 wherein outside walls of the first and second containers are color coded differently from one another.

6. A method according to claim 1 wherein each of the containers has its own pump mechanism for non-simultaneously dispensing each of the respective compositions.

7. A method according to claim 1 wherein the first and second compositions provide a benefit selected from the group consisting of cleansing, moisturizing, toning, anti-wrinkling, sunscreening, self-tanning foundation covering and mixtures thereof.

8. A method according to claim 1 wherein the first and second compositions independently include an active material selected from the group consisting of alpha-hydroxycarboxylic acid or salts thereof, beta-hydroxycarboxylic acids or salts thereof, sunscreens, retinoids, ceramides, surfactants, self-tanners and mixtures thereof.

9. A method according to claim 1 further comprising instructing consumers, by placing on the containers or packaging associated therewith instructions on use of the first and second compositions together in a sequential manner to achieve the first and second benefits in a treatment regime.

10. A skin treatment regime product comprising:

a first composition containing at least one first active within a first pharmaceutically acceptable carrier, the first composition functioning to impart a first benefit to the skin;

a second composition containing at least one second active within a second pharmaceutically acceptable carrier, the second composition functioning to impart a second benefit to the skin;

a first container for storing the first composition;

a second container for storing the second composition, the first and second containers being joined together wherein the outside walls of the first and second containers are color coded differently from one another; and instructions for consumers placed on the containers or packaging associated therewith on use of the first and second compositions in a sequential manner to achieve the first and second benefits in a treatment regime, the first and second compositions being complementary products.

* * * * *